US 6,612,837 B2

United States Patent
Schostek et al.

(10) Patent No.: US 6,612,837 B2
(45) Date of Patent: Sep. 2, 2003

(54) DENTAL MILLING INSTRUMENT

(75) Inventors: Gerd Schostek, Gelnhausen (DE); Hartmut Brinkmann, Bohmte (DE); Klaus-Dietrich Lingemann, Osnabrück (DE); Axel Höh, Bohmte (DE)

(73) Assignee: Degussa Dental GmbH, Hanau (DE)

( * ) Notice: Subject to any disclaimer, the term of this patent is extended or adjusted under 35 U.S.C. 154(b) by 0 days.

(21) Appl. No.: 09/827,318

(22) Filed: Apr. 6, 2001

(65) Prior Publication Data

US 2001/0044093 A1 Nov. 22, 2001

(30) Foreign Application Priority Data

Apr. 7, 2000 (DE) .......................... 100 17 474

(51) Int. Cl.$^7$ ................................ A61C 3/06
(52) U.S. Cl. .......................... 433/51; 408/35; 408/237
(58) Field of Search ................. 433/50, 51 OR, 433/52, 75, 76, 213; 408/35, 236, 237

(56) References Cited

U.S. PATENT DOCUMENTS

| 4,190,938 A | * | 3/1980 | Hillmann | 408/35 |
| 4,478,580 A | | 10/1984 | Barrut | 433/223 |
| 4,941,826 A | * | 7/1990 | Loran et al. | 433/51 |
| 5,213,454 A | * | 5/1993 | Gilver et al. | 408/61 |

FOREIGN PATENT DOCUMENTS

| DE | 25 23 126 | | 12/1976 | |
| DE | 7908672 | | 9/1979 | |
| DE | 3611518 | | 10/1987 | |
| DE | 4012327 | | 10/1991 | |
| FR | 2545744 | * | 3/1984 | 408/237 |

* cited by examiner

Primary Examiner—John J. Wilson
(74) Attorney, Agent, or Firm—Smith, Gambrell & Russell, LLP

(57) ABSTRACT

A dental milling instrument includes a base connected to a guide column for a vertically adjustable milling arm which receives a milling unit. The milling arm can be displaced by its supporting slide along a guideway of the guide column, by means of an electromotive height-adjusting drive. A threaded spindle, capable of being driven by an adjusting motor, is in engagement in a backlash-free and self-locking manner with a spindle nut provided in the supporting slide. Vertical positioning and vertical fixation are accomplished entirely from an operating panel provided on the base.

9 Claims, 1 Drawing Sheet

DENTAL MILLING INSTRUMENT

BACKGROUND OF THE INVENTION

1. Field of the Invention

The invention relates to a dental milling instrument having a base which supports a working table, the base being connected to a guide column for a vertically adjustable milling arm which receives a milling unit.

2. Description of the Related Art

When milling and drilling operations are performed on dental objects, in particular on dental casts and prosthodontic parts, in addition to the horizontal positioning of the milling or drilling tools, it is necessary also to adapt the vertical position of the tools to the heights of the various workpieces. It is frequently also necessary to reassume a previous, defined vertical position after a height adjustment of the milling arm.

In the dental milling instruments known today, this height adjustment is typically accomplished manually via toothed racks or threaded spindles on a central guide column. In the case of a known dental milling instrument (DE 36 11 518 C2), the guide column is rotatably supported on the base. The milling arm is guided on the guide column so as to be vertically adjustable and capable of being clamped in place by means of a hand lever. The swivelling guide column is capable of being locked on the base by means of a locking screw. With a view to height adjustment, the milling arm has to be displaced manually on the guide column, in which connection a helical screw serves for weight compensation. In order to attain the requisite stiffness and precision for the subsequent milling and drilling operations in a given case, an actuation of the various fixing devices is necessary after the adjustment. The operating elements of these fixing devices are frequently arranged at places on the milling instruments which are spaced far apart from one another, consequently constraining the user to a mode of operation that is not very ergonomic. The clamping forces obtained by such fixing devices depend on the manual force applied by the user, and are consequently undefined, which can lead to inaccuracies in the subsequent working steps.

For various working processes, it may be necessary to regain a defined vertical position after a vertical displacement of the milling arm. To this end, use is generally made of manually adjustable stops on the vertical guide. These mechanical stops must be kept clean at all times, since, for example, metal chips which might fall on them can impair the accuracy of the positioning.

It is therefore an object of the present invention to design a dental milling instrument in such a way that a vertical adjustment can be carried out in a simple manner, without adjusting levers, adjusting handwheels or clamping levers having to be manually actuated for the purpose.

SUMMARY OF THE INVENTION

The present invention provides a dental milling instrument with a milling arm which can be displaced along a guideway of the guide column, by means of an electromotive height-adjusting drive.

In the present invention, vertical adjustment is accomplished exclusively by actuation of an electrical switch, for example a pushbutton switch, in an operating panel that can be easily accessed by the user. The vertical fixation can be guaranteed, for example, by the holding moment of the electric adjusting motor.

The height-adjusting drive according to the invention preferably comprises a screw link actuator which can be driven by an electric adjusting motor, and which preferably comprises a threaded spindle which is supported in the base, and which is in engagement with a spindle nut on the milling arm. Hence the electromotive adjusting drive is realised in a device that is simple to construct and saves space.

According to a preferred embodiment, the invention is provided with a screw link actuator of self-locking construction. Hence, a vertical fixation of the milling arm on the guide column is obtained automatically in the currentless state.

With a view to achieving a precise vertical position, it is preferred that the screw link actuator can be set so as to prevent backlash.

The electric adjusting motor according to the invention is preferably a stepping motor. From the number of steps of the motor, the vertical position that is attained in a given case can then be identified and pre-specified by an electric control unit. The control device for the stepping motor supplies a position signal which is derived from the number of steps of the motor, and which corresponds to the vertical position of the milling arm to an indicating and/or positioning device. A set position can be stored in the positioning device of the control device and reassumed at will.

It is possible instead that the milling arm comprises a pickup for a digital, displacement-measuring device which is connected to the guide column, and which supplies a position signal corresponding to the vertical position of the milling arm to the indicating and/or positioning device.

Further preferred configurations of the inventive concept are the subject of the claims of the application. Additional variations and modifications will be apparent to those skilled in the art.

BRIEF DESCRIPTION OF THE DRAWINGS

The invention will be better understood with reference to the accompanying drawing, in which.

DETAILED DESCRIPTION OF THE INVENTION

Figure 1:
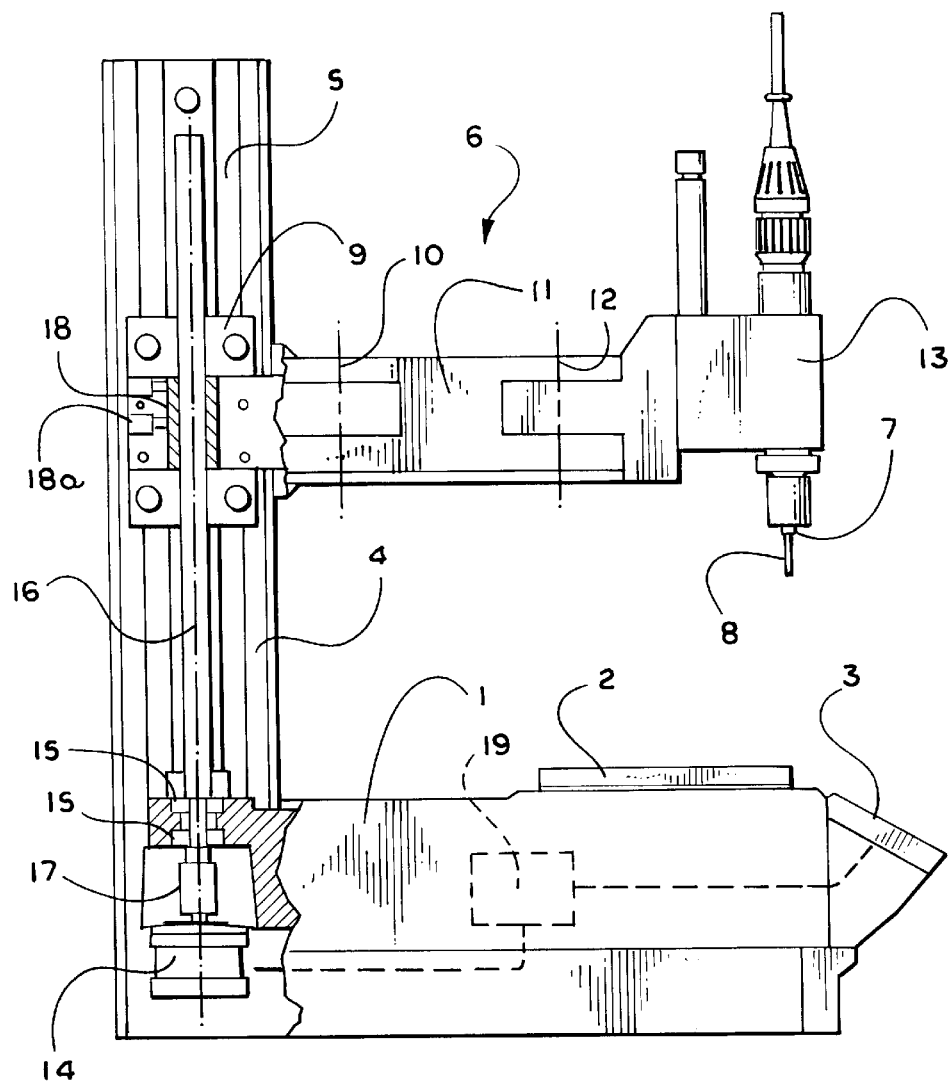
FIG. 1 depicts an embodiment of the dental milling instrument of the invention in a side view, and partially in section.

The accompanying drawing shows a dental milling instrument in a side view and partially in section. A base 1 supports a working table 2 and an electrical operating panel 3. The working table 2 serves to receive the dental objects to be processed. The base 1 is connected to a vertical guide column 4 which comprises a guideway 5 for an articulated milling arm 6 which supports a milling unit 7 in which an interchangeable milling or drilling tool 8 is received. The milling arm 6 comprises a supporting slide 9 which can be displaced along the guideway 5 of the guide column 4. The supporting slide 9 is connected in a horizontally swivelling manner to a middle portion 11 of the milling arm via a first vertical swivel axis 10. The middle portion 11 of the milling arm is connected in swivelling manner to a support 13 for the milling unit 7 via a second vertical swivel axis 12.

The vertical movement and vertical positioning of the milling arm 6 are effected by means of an electromotive height-adjusting drive which includes a screw link actuator, comprising a threaded spindle 16 and a spindle nut 18, capable of being driven by an electric adjusting motor 14. A threaded spindle 16 which is supported in bearings 15 in the base 1, and which extends along the vertical guide column 4, is connected to the adjusting motor 14 via a coupling 17. The threaded spindle 16 is in engagement with a spindle nut 18 which is arranged in the supporting slide 9. The spindle nut 18 can be set in a backlash-free manner by means of a setting screw 18a.

In the embodiment example presented, the adjusting motor 14 is a stepping motor controlled by a control device 19, which is connected to the operating panel 3 as an indicating and/or positioning device. Via a pushbutton switch in the operating panel 3, it is possible for the adjusting motor 14 to be driven and hence for the milling arm 6 to be displaced vertically. The respective vertical position is calculated by the control unit 19 from the number of steps of the motor. The vertical fixation of the milling arm 6 is guaranteed by the holding moment of the adjusting motor 14, which is constructed as a stepping motor, and by the self-locking of the screw link actuator 16, 18.

Via an appropriate button in the operating panel 3, it is possible for the milling arm 6 to be raised vertically by a pre-specified distance, for example in order to change the drilling or milling tool 8. By repeated actuation of a button in the operating panel 3, the milling arm 6 is again lowered into the initial position which was stored previously in the electronic control device 19.

The vertical movement and vertical fixation of the milling arm 6 are in this case controlled exclusively from the operating panel 3. Additional grips in the region of the guide column 4 are dispensed with. Hence an ergonomic workplace is guaranteed, and reliable fixation does not depend on the manual force applied by the user.

Further variations and modifications will be apparent to those skilled in the art from the foregoing, and are intended to be encompassed by the invention according to the claims which follow.

German priority application 100 17 474.4 is relied on and incorporated herein by reference.

We claim:

1. A dental milling instrument, comprising:
   a base, which supports a work table of the dental milling instrument;
   a guide column, attached to the base, provided with a guideway along which a milling arm is vertically displaceable;
   a supporting slide connected in a swivelling manner to a middle portion of the milling arm via a first vertical axle, and wherein the middle portion of the milling arm is connected in a swiveling manner to a support for a milling unit via a second vertical swivel axle, and
   an electromotive height-adjusting drive, comprising a screw link actuator driven an electric adjusting motor, which vertically displaces the milling arm along the guideway of the guide column.

2. The dental milling instrument according to claim 1, wherein the screw link actuator comprises:
   a threaded spindle, provided along the guideway of the guide column; and
   a spindle nut, provided on the milling arm, which is engaged with the threaded spindle.

3. The dental milling instrument according to claim 2, wherein the threaded spindle is supported in the base of the dental milling instrument.

4. The dental milling instrument according to claim 1, wherein the screw link actuator is of self-locking construction.

5. The dental milling instrument according to claim 1, wherein the screw link actuator can be set to prevent backlash in operation.

6. The dental milling instrument according to claim 1, wherein the electric adjusting motor is a stepping motor.

7. The dental milling instrument according to claim 6, wherein a control device for the stepping motor supplies a position signal derived from the number of steps of the motor, which number of steps of the motor is interpreted by an indicating or positioning device to correspond to a vertical position of the milling arm.

8. The dental milling instrument according to claim 1, wherein the milling arm is provided with a pickup for a digital displacement-measuring device, connected to the guide column, which supplies a position signal which is interpreted by an indicating or positioning device to correspond to a vertical position of the milling arm.

9. The dental milling instrument according to claim 1, wherein the milling arm comprises a supporting slide by which the milling arm is displaceable along the guideway of the guide column.

* * * * *